United States Patent [19]

Cysewski et al.

[11] 4,417,415
[45] Nov. 29, 1983

[54] PROCESS FOR CULTURING A MICROALGA, AND EXTRACTING A POLYSACCHARIDE THEREFROM

[75] Inventors: Gerry R. Cysewski, Snoqualmie; Daniel B. Anderson, Pasco, both of Wash.

[73] Assignee: Battelle Development Corporation, Columbus, Ohio

[21] Appl. No.: 371,868

[22] Filed: Apr. 26, 1982

[51] Int. Cl.³ .............................................. A01G 7/00
[52] U.S. Cl. ....................................... 47/1.4; 435/101
[58] Field of Search ............................ 47/1.4; 435/101

[56] References Cited

U.S. PATENT DOCUMENTS

| | | | |
|---|---|---|---|
| 349,760 | 9/1886 | Stanford et al. | |
| 1,184,981 | 7/1965 | Thornley et al. | |
| 3,195,271 | 7/1965 | Golueke et al. | 47/1.4 |
| 3,396,158 | 8/1968 | Hang | 260/209.6 |
| 3,879,890 | 4/1975 | Chen et al. | 47/1.4 |
| 3,900,462 | 8/1975 | Komatani et al. | 260/209 R |
| 4,078,331 | 3/1978 | Savins et al. | 47/1.4 |
| 4,078,332 | 3/1978 | Savins | 47/1.4 |
| 4,079,544 | 3/1978 | Savins | 47/1.4 |
| 4,087,936 | 5/1978 | Savins et al. | 47/1.4 |
| 4,202,969 | 5/1980 | Ueno et al. | 536/1 |
| 4,225,673 | 11/1980 | Sugiura et al. | 435/101 |
| 4,236,349 | 12/1980 | Ramus | 47/1.4 |

OTHER PUBLICATIONS

Kirk-Othmer's Encyclopedia of Chemical Technology (2nd Edition, 1968), vol. 17, pp. 763 14 784.
Medcalf, et al., Carbohydrate Research 44, 87-96 (1975).
Proceedings of the Eighth International Seaweed Symposium, 583-588 (1981).
R. F. Jones, Journal of Cellular and Comparative Physiology (1962), pp. 61-64.
Percival, et al., Carbohydrate Research 72, 165-176 (1979).
Aquaculture and Algae Culture, Food Technology Review No. 53, Noyes Data Corporation, 1979, pp. 254-264.

*Primary Examiner*—Robert E. Bagwill
*Attorney, Agent, or Firm*—Barry S. Bissell

[57] ABSTRACT

*Porphyridium cruentum* is cultured in an enriched seawater medium using a high initial cell concentration until the productivity of polysaccharide production by the alga is maximized. The whole culture is then extracted by making the culture strongly alkaline, and heat treating it. The culture is cooled, acidified and the polysaccharide precipitated by addition of a water-miscible organic solvent such as ethanol. Very high yields of polysaccharide are obtained, in excess of 4.5 grams per liter of culture.

38 Claims, 1 Drawing Figure

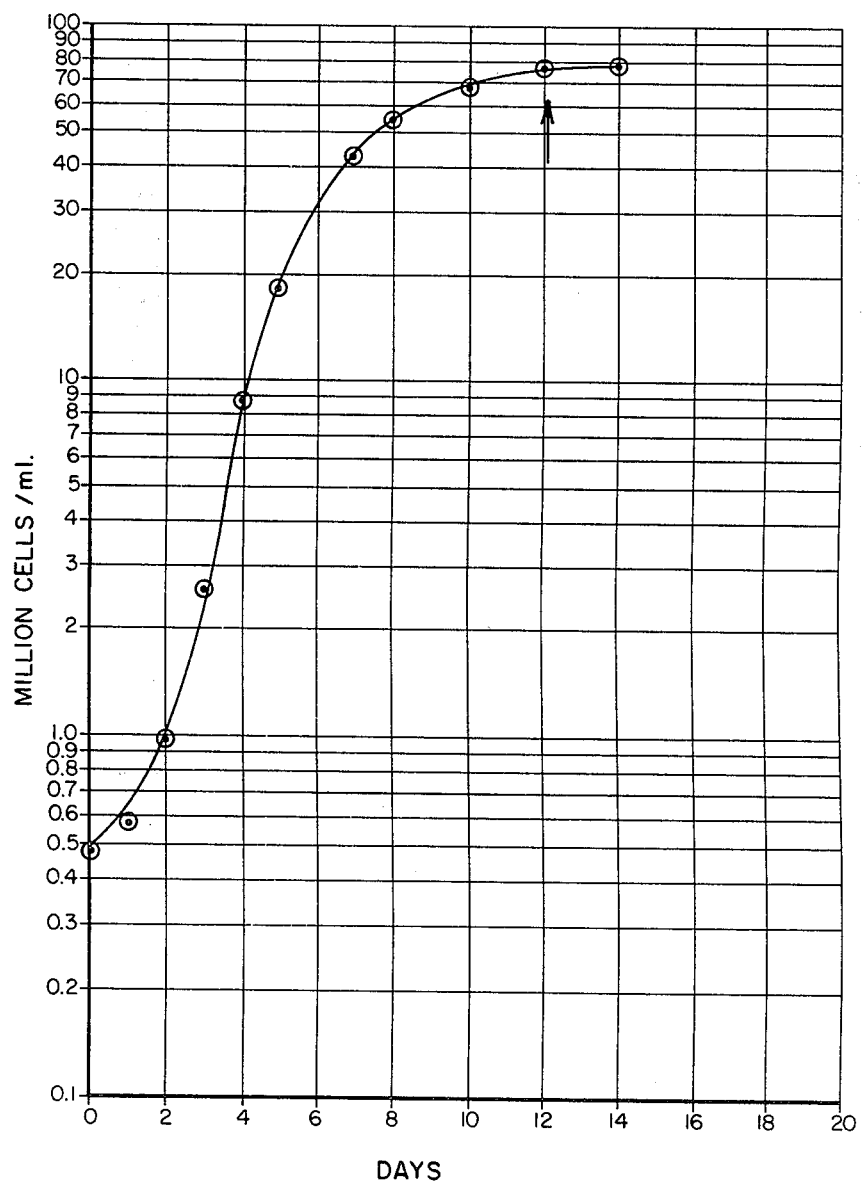

PROCESS FOR CULTURING A MICROALGA, AND EXTRACTING A POLYSACCHARIDE THEREFROM

BACKGROUND OF THE INVENTION

The invention relates to a process for culturing a microalga and for extracting a polysaccharide therefrom.

For many years, hydrophilic colloidal polysaccharides, such as agar, algin, carrageenan, furcellaran and funoran, have been extracted from marine macroalgae (seeweeds). These polysaccharides are useful as thickeners, gelling agents, emulsion stabilizers, suspending agents, emollients and demulcents and are used in large quantities in the food, cosmetics and pharmaceutical industries. Polysaccharides are also used in the oil industry as thickeners in drilling muds and in fluids used for the tertiary recovery of oil from underground strata. It is estimated that the total value of polysaccharides produced from seaweeds in the United States in currently about two hundred million dollars per year.

However, the recovery of polysaccharides from macroalgae is attended by numerous difficulties. It is not practical to artificially culture macroalgae on the scale necessary for large-scale polysaccharide production, due to their large size and the resultant space required. Accordingly, the macroalgae must be harvested from their natural sites in shallow water near to sea coasts. Many of the coasts on which the macroalgae occur are rocky and are subject to severe storms at certain times of the year. The growth of the macroalgae in various parts of the United States is hindered by over-harvesting, coastal water pollution, sea urchin infestation and other factors. Moreover, the labor involved in harvesting natural macroalgae is difficult arduous and expensive. Furthermore, the macrolagae may be contaminated by large amounts of foreign matter, such as sand, and require considerable pretreatment to remove such foreign matter before the polysaccharide is extracted from the macroalgae. It is difficult to produce a consistent product from macroalgae and it is necessary to monitor very closely the properties of the polysaccharide, and often to blend polysaccharide from different batches of seaweed, in order to ensure that the thickening properties of the polysaccharide remain constant, since such properties vary not only with the type of seaweed and the site on which it grows, but also with the time of the year. Finally, a considerable portion of the world's macroalgae resources are located in countries of dubious political stability, so that the international trade in macroalgae polysaccharides is vunerable to interruptions for political reasons.

In view of the difficulties associated with the production of polysaccharides from macroalgae, attempts have recently been made to extract such polysaccharides from microalgae, several of which are known to exude polysaccharides into the medium surrounding them at various stages during their life cycle; see, for example, Percival and Foyle, Extracellular Polysaccharides of *Porphyridium cruentum* and *Porphyridium aerugineum*, Carbohydrate Research 72, 165–176 (1979). U.S. Pat. No. 4,087,936, issued May 9, 1978 to J. G. Savins and M. L. Anderson, describes a process for the extraction of a polysaccharide from *P. cruentum*. This process is carried out in fermentation vessels using either artificial light or sunlight and thus the process can be much better controlled than can a process using marine macroalgae. Such processes using microalgae under closely controlled conditions can be expected to yield a much more uniform product than is usually obtained from marine macroalgae.

Unfortunately, the yields of polysaccharide from microalgae cultures have hitherto been disappointing. For example, Medcalf et al., Carbohydrate Research 44, 87–96 (1975) report a yield of only 0.47 g. of polysaccharide per liter of culture medium containing *P. cruentum*. Such low yields would render the resultant polysaccharide uncompetitive with comparable polysaccharides isolated from marine macroalgae.

We have now concluded that one of the reasons for the previously-reported low yields of polysaccharides from microalgae is that previous processes have concentrated their efforts on maximizing the amount of extracellular polysaccharide produced and have been concerned mainly with the extraction of the extracellular polysaccharide; for example, in the aforementioned U.S. Pat. No. 4,087,936, the culture medium containing the microalgae is centrifuged to remove the cells therefrom and only the cell-free growth medium is used.

SUMMARY OF THE INVENTION

Our process comprises culturing the marine alga *Porphyridium cruentum* under conditions designed to maximize the total production of polysaccharide, without regard to whether such polysaccharide is intracellular or extracellular. The entire alga culture is then treated to obtain both the intracellular and extracellular polysaccharide therefrom. We have found that most of the polysaccharide in a culture of *P. cruentum* is retained within the microalgal cells and the attached polysaccharide capsule. Thus, by extracting the entire culture, we can obtain yields several times those obtained by prior workers.

The culturing stage of our processes uses a growth medium comprising seawater having added thereto sufficient soluble nitrate and soluble phosphate to make the solution at least about 0.015 M in nitrate and 0.0012 M in phosphate. Preferably the nitrate concentration is about 0.03 M and the phosphate concentration is about 0.0018 M. The growth medium is adjusted to an initial pH in the range of about 7.3 to about 8.3; it is not necessary to control the pH during the culturing process. To this growth medium, there is added an inoculum of *P. cruentum* sufficient to provide an initial cell concentration of at least about 100,000 cells/ml. of the growth medium and the inoculated growth medium is then cultured at a temperature in the range of about 18° to about 24° C. and in the presence of light. During the culturing of microalga, an oxygen-containing gas including a minor proportion of carbon dioxide is passed through the culture medium. The culturing is desirably continued until the maximum total polysaccharide is attained; this typically takes 10–16 days.

To extract the polysaccharide from the culture, the culture is brought to a pH of about 10 to about 14 and is heated to at least about 80° C. for at least about 20 minutes. The culture is then cooled to not more than about 40° C. and made nonalkaline with acid. After the addition of the acid, a water-miscible organic solvent is added to the culture in an amount sufficient to cause polysaccharide to precipitate therefrom and the resultant precipitated polysaccharide is separated from the accompanying liquid.

It should be noted that, although reference has been made above to precipitation of the polysaccharide from the culture, the polysaccharide is less dense than the liquid (either inherently or because of entrained gases) and thus will tend to float on the liquid. It is in that sense that the term "precipitation" is used throughout this application.

BRIEF DESCRIPTION OF THE DRAWING

The FIGURE shows a typical cell growth curve obtained using the instant culture process; note that the ordinate scale is logarithmic.

DETAILED DESCRIPTION OF THE INVENTION

In the preferred variant of the instant culture method, an enriched seawater growth medium is used. To prepare this growth medium, natural seawater is preferably filtered through a 0.5 μm. filter and to the filtered seawater are added sufficient nitrate and soluble phosphate to make the solution about 0.03 M in nitrate and 0.0018 in phosphate. Micronutrients should also be added as shown in the following Table:

| Micronutrient | Concentration mg/l |
|---|---|
| $ZnCl_2$ | 0.0105 |
| $H_3GO_3$ | 0.00039 |
| $CuCl_2.2H_2O$ | 0.0089 |
| $MnCl_2.4H_2O$ | 0.01049 |
| $(NH_4)_6Mo_7O_{24}.4H_2O$ | 0.096 |
| $FeCl_2.6H_2O$ | 0.525 |

The seawater is adjusted to a pH in the range of about 7.3 to about 8.3, most desirably 7.8, by the addition of alkali, preferably potassium hydroxide. The culture medium does not need to be autoclaved, since we have found that *P. cruentum* is very resistant to microbial contamination, and thus bacteria do not flourish and do not cause serious interferences with the culture process.

Contrary to the statement in U.S. Pat. No. 3,195,271, it is not necessary to include sewage in the growth medium to ensure proper growth of *P. cruentum* and indeed it is very much preferred that sewage not be added to the growth medium since unwanted contaminants may be introduced therewith.

We prefer to add the nitrate to the growth medium as sodium nitrate and the phosphate as potassium dihydrogen orthophosphate though other soluble nitrates and orthophosphates may be used provided, of course, that they are not toxic to the alga. If it is desired to carry out the instant culture process in a place where seawater is not readily available, the growth medium may be made up from "artificial seawater" prepared by dissolving appropriate quantities of the necessary salts in water. Unless otherwise specified, the term "seawater" as used herein is to be construed as including such artificial seawater. However, natural seawater appears to give the best results. *P. cruentum* is a marine microalga, and natural seawater may contain presently-unknown constituents which aid its growth.

After the growth medium has been thus prepared, there is added thereto an inoculum of *P. cruentum* sufficient to provide an initial cell concentration of at least about 100,000 cells/ml. of the growth medium and preferably more. The size of the inoculant is important in that the larger the inoculant, the faster the culture will reach a high cell density. Also, at low cell densities the alga is likely to become bleached under the intense lighting levels we prefer to use in the culturing process (see below). We prefer to use an inoculum of sufficient size to provide an initial cell density of at least about 400,000 cells/ml. of the growth medium. The preferred strain of *P. cruentum* for use in the instant process is *P. cruentum* #161, obtainable from the culture collection of the University of Texas at Austin, Tex. The inoculum of *P. cruentum* does not have to be axenic.

Following this inoculation, the growth medium is cultured at a temperature in the range of about 18° to about 24° C., and preferably at 20°-22° C. To enable the photosynthetic alga to grow, it is of course necessary that the medium be illuminated during culture; the necessary illumination can be either sunlight or artificial light, although for obvious reasons, to ensure the maximum growth rate it is desirable to provide artificial light during the periods when sunlight is not present. To ensure the algae obtains sufficient light, the culture is preferably effected in a vessel providing a fairly large ratio of surface area to volume, e.g. 0.01 $m^2$ of surface area per liter of growth medium, and at least 10,000 lux of light should be provided on this surface area. On an experimental scale, we have found that a vessel containing 10 liters of growth medium and providing a surface area of 0.2 $m^2$ illuminated by twenty-four 15 watt fluorescent tubes adjacent the culture surface (thus providing an intensity of 19375 lux evenly over the entire surface) gives very satisfactory growth rates. This vessel is an agitated fermenter.

In large-scale production facilities, it may be desirable to use vessels having a lower area: volume ratio, a higher light intensity and/or more intensive agitation.

During culturing, the alga requires access to both oxygen and carbon dioxide. Accordingly, an oxygen-containing gas containing a minor proportion of carbon dioxide should be passed through the growth medium during culturing. The preferred oxygen-containing gas for this purpose is air containing at least about 3% of carbon dioxide. In the experimental culture vessel already mentioned containing 10 liters of growth medium, this air/carbon dioxide mixture is preferably passed at about 9 liters/minute. Although the initial pH of growth medium should be adjusted within the limits already mentioned, it is not necessary to control the pH during culturing, since the growth of the microalga does not significantly alter the pH.

The culturing is preferably continued until just before the growth of the *P. cruentum* becomes nutrient limited, mainly nitrate limited. When the alga reaches this nutrient limited stage, usually at cell densities of 50–75 million cells/ml., the alga exudes polysaccharide at an accelerated rate and, if the culture is allowed to stand, it thickens and ultimately bleaches from red to brown to light tan. At the onset of the nutrient limited, "stationary" phase, during which little further multiplication of the cells takes place, the polysaccharide productivity of the culture is substantially at its maximum value; although further culturing may increase the total polysaccharide concentration slightly, this increase in polysaccharide concentration is not sufficient to make further culturing economically worthwhile. It is desirable to terminate culturing at this point and to proceed with the extraction of the polysaccharide. Further calling does not significantly increase the total polysaccharide present but does increase the amount exuded through the cell walls, which may undesirably increase the viscosity of the culture.

Once culturing has been completed, the entire culture medium, including both the cells and the liquor, is subjected to the polysaccharide extraction process. As stated above, we have found that much higher yields of polysaccharide can be obtained by extracting the whole culture medium rather than by prior art processes which only use the extracellular polysaccharide. We have found that most of the polysaccharide is contained within the cells or in the mucilaginous sheath attached to the cells. By extracting the entire culture, the extracellular, intracellular and sheath polysaccharide can all be recovered, greatly increasing the overall yield. We have found that by the instant extraction process yields of polysaccharide in excess of about 4.5 g/l of growth medium can be achieved.

In the first stage of the polysaccharide extraction phase of the process, the pH of the culture is raised to about 10 to about 14. Preferably, a concentrated aqueous sodium hydroxide solution is added to the culture in an amount sufficient to add 20 g/l of sodium hydroxide to the culture, thereby raising the pH to about 13.6. It is then desirable to agitate the culture gently by mechanical stirring or an air sparge to ensure thorough mixing with the alkali.

After the solution has been made alkaline, it is heated to a temperature of at least about 80° C. for a period of at least about 20 minutes. We prefer to heat the culture to a temperature of about 90° to about 100° C. for a period of about 30 to about 60 minutes, although in some cases this heating can usefully be continued for up to 3 hours. During this heat treatment step, agitation is not essential although mild agitation may be useful in enhancing the efficacy of the extraction process.

At the end of this heating step, the culture is usually strongly colored and contains clumps of polysaccharide. The culture is then cooled to a temperature of not more than about 40° C., and preferably not more than about 30° C., and neutralized with acid. The acid used should be a mineral acid and is preferably concentrated hydrochloric acid. We prefer not only to neutralize the culture but to render it strongly acid, below pH 2 and preferably about pH 1, to obtain the purest product. After acidification, the culture is desirably gently agitated by mechanical stirring or an air sparge until all the white clumps of crude polysaccharide material go into solution. On some occasions, a small amount of insoluble material may remain in the acidified culture; this material appears to be cellular debris and, if present, may easily be removed by filtration before the next step of the extraction process.

The polysaccharide is precipitated from the accompanying liquid by adding a water-miscible organic solvent in an amount sufficient to cause the polysaccharide to precipitate from the liquor. The preferred organic solvent for this purpose is ethanol, and desirably for about 2 to about 3 volumes of ethanol are added to each volume of the culture. Acetone methanol or isopropanol may also be used to precipitate the polysaccharide. The polysaccharide precipitates in the form of white fibers which clump together and float to the top of the liquor; if the culture has not been filtered before the precipitation step, any residue from the acidification step will remain at the bottom of the liquid and thus remain separate from the polysaccharide. The polysaccharide may be easily removed from the accompanying liquid by winding it onto a rod or by pouring the liquid through a screen mesh of approximately 1 mm. pore size.

After separation from the liquid, the crude polysaccharide is preferably squeezed to remove excess ethanol and water therefrom. Thereafter, the polysaccharide may be redissolved in water and reprecipitated by the addition of a water-miscible organic solvent in the manner already described. More desirably, the crude polysaccharide may be redissolved in a salt solution and reprecipitated by the addition of a water-miscible organic solvent in the manner already described. The use of a salt solution is preferred because, when water alone is used, the polysaccharide may be dispersed to such an extent that it is difficult to recover it. If the salt solution used is an aqueous solution of a calcium, sodium, potassium, zinc, copper or ferric iron salt, the physical form of the purified polysaccharide following reprecipitation with the organic solvent is much more desirable than when water alone is used for the redissolution of the crude polysaccharide.

In a particularly preferred technique, the crude polysaccharide is placed in a 2 M calcium chloride solution which is approximately one-half of the volume of the original culture extracted. The solution is then gently agitated and heated to 90° C. until all the crude polysaccharide dissolves. Then about 2 to about 3 volumes of ethanol are added to each volume of the solution to precipitate the white fibrous calcium salt of the polysaccharide. The calcium cation serves to form ionic bridges between the sulfate ester linkages present in the polysaccharide and thus aids in the precipitation thereof. The use of cations other than calcium affects the polysaccharide's rheological properties but such cations otherwise act in the same manner as calcium. The pure calcium salt of the polysaccharide may be easily removed from the accompanying liquid by winding it onto a stirring rod or pouring it through a screen.

The calcium salt is desirably squeezed to remove excess ethanol and water and dried, either in air at ambient temperature or, for greater speed of drying, at temperatures up to 45° C. under vacuum. The dried polysaccharide cake may then be ground to a fine tannish-white powder which is readily soluble in warm water. A 2% aqueous solution of the calcium salt forms a very viscous solution. Instead of treatment with a calcium salt, the crude polysaccharide obtained from the extraction process may be redissolved in water and purified by dialysis.

EXAMPLE I

An enriched seawater culture medium was prepared by filtering natural seawater through a 0.5 μm filter and adding sufficient sodium nitrate and potassium dihydrogen orthophosphate to make the seawater 0.015 M in nitrate and 0.0012 M in orthophosphate. To each liter of the seawater, there was then added 1 ml. of a micronutrient solution containing 7 mg/l. of zinc chloride, 0.26 mg/l. of boric acid, 5.9 mg/l. of cupric chloride dihydrate, 69.9 mg/l. of manganous chloride tetrahydrate, 64 mg/l. of $(NH_4)_6Mo_7O_{24} \cdot 4H_2O$ and 350 mg/l. of ferrous chloride dihydrate.

The enriched seawater medium thus prepared was adjusted to pH 7.8 with potassium hydroxide, and 10 l. of the culture medium placed in a 14 l. NBS Microferm fermenter having a surface area of 0.2 $m^2$ and capable of being illuminated by twenty-four 15 watt fluorescent tubes (thus providing an intensity of 19375 lux evenly over the surface). The fermenter was then inoculated with 200 ml. of a stock culture of *P. cruentum* #161, thus providing an initial cell density of 475,000 cells/ml.

The medium was cultured at 22° C., the pH is not being controlled after the initial adjustment. The culture was illuminated continuously, and small samples were taken daily to determine the cell concentration. In the later stages of culturing, larger samples of 100-200 ml. were taken for determination of the concentration of polysaccharide in the culture. The fermenter was continuously agitated.

On day 1 the culture was inoculated and the fermenter illuminated with only 12 of the 24 flourescent tubes. Air, not enriched with carbon dioxide, was passed through the fermenter at a flow rate of 4 l/min. On day 5, the lighting was increased by switching on 18 of the 24 tubes and when, on day 6, the samples indicated that the cell numbers were reaching the end of their exponential growth phase, the lighting was increased to full power, that is to say with all 24 tubes illuminated. On day 6, the cell density was $18.1 \times 10^6$ cell/ml., thus giving a specific growth rate through day 6 of 0.78 days$^{-1}$, representing a doubling time of 15 hours.

The accompanying drawing shows the actual cell densities achieved from days 0 to 6 of these experiments. The data beyond day 6 have been extrapolated on the assumption that the improvements suggested below were adopted. On this assumption, it can be expected that maximum cell density will be achieved within 14 days with a maximum polysaccharide concentration of 4.5 g/l and that the maximum polysaccharide productivity should be achieved by terminating the culturing after about 10-14 days depending upon the exact culturing technique used.

After 12 days, the culture was bleaching to a brownish color and cell density had leveled off at $41.5 \times 10^6$ cells/ml. Half the original amount of nitrate was added to the culture to replenish the nitrate concentration therein.

It was at day 12 that the taking of the larger samples for determination of the concentration of polysaccharide in the culture was commenced. All polysaccharide estimations were made by the procedure described in Example II, except that the crude polysaccharide was not redissolved in calcium chloride solution but in water prior to the final precipitation. Because redissolution in water rather than calcium chloride tends to give lower recovery of polysaccharide, the concentrations of polysaccharide in the culture reported below may tend to be below the true values.

The polysaccharide concentration in the solution on day 12 was determined to 1.99 g/l.

By day 15 the culture was again turning red. The flow of air through the fermenter was replaced by a flow of air to which 0.2% of carbon dioxide had been added and the gas flow rate was increased to 9 l/min., thus giving a carbon dioxide flow rate through the fermenter of 18 ml/min. The cell concentration was determined to be $40.0 \times 10^6$ cell/ml. and the polysaccharide concentration 2.3 gl.

On day 22, it was determined that the culture density had increased over the preceding seven days, but the culture was again turning brown. Half the original amount of nitrate and half the original amount of phosphate, together with half the original amounts of the micronutrients, were added to the culture to replenish the nutrients. The cell concentration was determined to be $52.0 \times 10^6$ cells/ml. and the polysaccharide concentration 4.14 g/l.

At day 27, the cell density had reached a maximum, but the culture remained bright red indicating that it was not nutrient-limited. The cell concentration was found to be $76.0 \times 10^6$ cells/ml. and the polysaccharide concentration 4.5 g/l., this being the maximum polysaccharide concentration in this experiment.

At day 32, the culture was beginning to turn brown again and no growth was occuring. The cell density was determined to $72.0 \times 10^6$ cells/ml. and the polysaccharide concentration 3.4 g/l. This polysaccharide yield was almost certainly low due to poor recovery of the polysaccharide in the extraction process without the use of a calcium cation; the true value would be expected to be at least as high as the 4.5 g/l. recorded on day 27.

On day 40, the culture had completely bleached to a tan-white color. Since there appeared to be no point in continuing further with this experiment, at this time the contents of the fermenter were transferred into a container for refrigerated storage and further analysis. After six months in refrigerated storage, the polysaccharide concentration was determined using the preferred extraction technique of the invention as described in Example II below.

EXAMPLE II

To the 10 l. of culture produced in Example I were added 200 gms. of sodium hydroxide in about 1 l. of water; this increased the pH of the culture to about 13.6. The sodium hydroxide solution was added slowly, with continuous mechanical stirring, to ensure through mixing with the culture.

The culture was then heated to 100° C. for 60 minutes with gentle mechanical stirring. After this heating, the culture was strongly colored and contained clumps of polysaccharide. The culture was then cooled to 30° C. and sufficient concentrated hydrochloric acid added to lower its pH to 1. Following the acidification, the culture was agitated with gentle mechanical stirring until all the clumps of polysaccharide had dissolved. 30 l. of ethanol were then added to the culture, causing the polysaccharide to separate from the liquor as white fibers which clumped together at the top of the liquor. The crude polysaccharide was separated from the liquor by filtration through a mesh screen of approximately 1 mm. pore size, and squeezed to remove excess ethanol and water therefrom.

The crude polysaccharide was then placed in 5 l. of 2 M calcium chloride solution, which was heated to 90° C., with gentle mechanical agitation until all the crude polysaccharide had dissolved. The solution was then cooled to ambient temperature and 15 l. of ethanol were added, thus precipitating the calcium salt of the polysaccharide. The salt was separated from the solution by filtration through the aforementioned mesh screen, squeezed to remove excess ethanol and water and dried at 40° C. under vacuum. The yield of the calcium salt of the polysaccharide was approximately 70 g. (7 g/l. of the original culture).

It was apparent from the difficulties experienced in the experimental procedure followed in Example I above, including especially the bleaching of the culture due to nutrient limitation, that the procedure described in Example I was not the optimum procedure for culture of the microalga. Based upon the problems experienced in Example I, we believe that for optimum culturing, the procedure described in Example I should be modified as follows:

A. In order to achieve rapid cell growth to the maximum density of about $76 \times 10^6$ cells/ml. and increased polysaccharide productivity, the initial concentrations of sodium nitrate and potassium dihydrogen also phosphate in the growth medium should be about 0.03 M and 0.0018 M respectively; similarly, the concentration of micronutrients should be about 1.5 times that used in Example I;

B. The air passed through the fermenter should at all times have 3–5% of carbon dioxide added thereto and the air flow rate should be 9 l/min. for the entire culturing period;

C. The maximum amount of light should be given to the culture as soon as possible i.e. the light intensity should be as high as possible provided that the culture is not bleached;

D. Continuous agitation is required in order to ensure that the culture receives good gas transfer and that all cells are brought into contact with the light; and E. The culture should be grown only until the maximum productivity is achieved, whereupon the entire culture should have the polysaccharide extracted therefrom immediately.

Based upon the foregoing conclusions, we believe that the best mode of carrying out the culture phase of our process at present known to us is that set forth in the following hypothetical Example III; we believe that the extraction process set forth above in actual Example II represents the best method for carrying out the extraction phase of our process at present known to us.

EXAMPLE III

An enriched seawater culture medium is prepared by filtering natural sea water through a 0.5 μm filter and adding sufficient sodium nitrate and potassium dihydrogen orthophosphate to make the seawater 0.015 M in nitrate and 0.0018 M in orthophosphate. To each liter of the seawater, there is then added 1 ml. of a micronutrient solution containing 10.5 mg/l. of zinc chloride, 0.39 mg/l. of boric acid, 8.9 mg./l of cupric chloride dihydrate, 104.9 mg./l. of manganous chloride tetrahydrate, 96 mg/l. of $(NH_4)_6Mo_7O_{24}.4H_2O$ and 525 mg./l. of ferrous chloride dehydrate.

The enriched seawater medium thus prepared is adjusted to pH 7.8 with potassium hydroxide and 10 l. of the culture medium are placed in the same fermenter as described in Example I above and inoculated in the same manner. The medium is then cultured at 22° C., the pH not being controlled after the initial adjustment. The culture is illuminated continuously and air containing 4% of carbon dioxide is passed continuously through the fermenter at a rate of 9 l/min., the fermenter being agitated continuously. After approximately 12 days the cell density should have reached a maximum of about $76 \times 10^6$ cell/ml. without bleaching, at which point the entire culture is subjected to the extraction procedure set forth in Example II above.

Although the extraction process just described is intended primarily for use with *P. cruentum*, it is believed that the process will also be satisfactory for extraction of a similar polysaccharide from *P. aerugineum*, which is known to exude polysaccharide; see the paper in *Carbohydrate Research* 72, 165–176 (1969) mentioned above. Obviously, the optimum culture conditions for *P. aerugineum* differ from those for *P. cruentum*, since the former is a fresh water alga. The extraction process may also be used to extract polysaccharide from the algae *Chlamydomonas mexicana* and *Arabaena CR-91*.

It will be apparent to those skilled in the art that numerous changes and modifications may be made in the preferred embodiments of the invention described above without departing from the scope of the invention. Accordingly, the foregoing description is to be construed in an illustrative and not in a limitative sense, the scope of the invention being defined solely by the appended claims.

We claim:

1. A process for extracting a polysaccharide from a culture of *Porphyridium cruentum*, said process comprising:
   (a) bringing said culture to a pH in the range of about 10 to about 14;
   (b) heating said culture to a temperature of at least about 80° C. for a period of at least about 20 minutes;
   (c) cooling said culture to a temperature of not more than about 40° C. and reducing the pH thereof to not greater than about 7;
   (d) adding to said cooled and non-alkaline culture a water-miscible organic solvent in an amount sufficient to cause said polysaccharide to precipitate from said culture; and
   (e) separating said precipitated polysaccharide from the accompanying liquid.

2. A process according to claim 1 wherein, in step (b), said culture is heated to a temperature of about 90° to about 120° C. for a period of about 30 to about 60 minutes.

3. A process according to claim 1 wherein, in step (c), said culture is cooled to a temperature of not more than about 30° C.

4. A process according to claim 1 wherein, in step (c), the pH of said culture is reduced to below about 2.

5. A process according to claim 1 wherein, in step (d), said water-miscible organic solvent is ethanol.

6. A process according to claim 5 wherein, in step (d), from about 2 to about 3 volumes of ethanol are added to each volume of said culture.

7. A process according to claim 1 wherein, in step (d), said water-miscible organic solvent is acetone, methanol or isopropanol.

8. A process according to claim 1 wherein, after step (e), the precipitated polysaccharide is redissolved in water and thereafter there is added to the resultant polysaccharide solution a water-miscible organic solvent in an amount sufficient to reprecipitate said polysaccharide from said solution.

9. A process according to claim 1 wherein, after step (e), the precipitated polysaccharide is redissolved in an aqueous solution of a salt of a metal selected from the group consisting of calcium, sodium, potassium, zinc, copper and ferric iron, and thereafter there is added to the resultant polysaccharide solution a water-miscible organic solvent in an amount sufficient to precipitate a metal salt of the polysaccharide therefrom.

10. A process according to claim 9 wherein said water-miscible organic solvent used to effect said precipitation of said metal salt is ethanol.

11. A process according to claim 10 wherein from about 2 to about 3 volumes of ethanol are added to each volume of the solution containing said polysaccharide and said metal salt.

12. A process according to claim 9 wherein said water-miscible organic solvent used to effect said precipitation of said metal salt is acetone, methanol or isopropanol.

13. A process according to claim 9 wherein said metal is calcium.

14. A process according to claim 13 wherein said metal salt is calcium chloride.

15. A process according to claim 14 wherein said polysaccharide is dissolved in an aqueous solution of calcium chloride heated to at least 80° C. under agitation and thereafter from about 2 to about 3 volumes of ethanol are added to each volume of said solution to precipitate said metal salt of said polysaccharide therefrom.

16. A process for culturing *Porphyridium cruentum* which comprises:
   (a) establishing a growth medium comprising seawater having added thereto sufficient soluble nitrate and phosphate to make the solution at least about 0.015 M in nitrate and 0.0012 M in phosphate, said growth medium having a pH in the range of about 7.3 to about 8.3;
   (b) adding to said growth an inoculum of *P. cruentum* sufficient to provide an initial cell concentration of at least about 100,000 cells/ml. of said growth medium; and
   (c) culturing said inoculated growth medium at a temperature in the range of about 18° to about 24° C. and in the presence of light while passing through said medium an oxygen-containing gas containing a minor proportion of carbon dioxide.

17. A process according to claim 16 wherein said growth medium is adjusted to a pH of about 7.8 before said inoculum is added thereto.

18. A process according to claim 16 wherein said inoculum is sufficient to provide an initial cell concentration of about 400,000 cells/ml. of said growth medium.

19. A process according to claim 16 wherein said culturing is effected in a vessel providing at least about 0.01 $m^2$ of surface area per liter of said medium and at least 10,000 lux of light are provided on said surface area.

20. A process to claim 16 wherein said oxygen-containing gas is air having from about 3 to about 6% by volume of carbon dioxide added thereto.

21. A process according to claim 16 wherein said culturing is continued for a period of from about 10 to about 16 days.

22. A process according to claim 16 wherein said nitrate in said growth medium is supplied as sodium nitrate and said phosphate as potassium dihydrogen orthophosphate.

23. A process according to claim 16 wherein said growth medium is made about 0.03 M in nitrate and about 0.0018 M in phosphate.

24. A process according to claim 16 wherein, after said culturing is completed, polysaccharide is extracted from the culture by a process comprising:
   (d) bringing said medium to a pH in the range of about 10 to 14; heating said medium to a temperature of at least 80° C. for a period of at least about 20 minutes; cooling said medium to a temperature of not more than about 40° C. and reducing the pH thereof to a value not greater than about 7;
   (e) adding to said cooled and non-alkaline medium a water-miscible organic solvent in an amount sufficient to precipitate said polysaccharide from said medium; and
   (f) separating said precipitated polysaccharide from the accompanying liquid.

25. A process according to claim 24 wherein, in step (d), said culture is heated to a temperature of about 90° to about 120° C. for a period of about 30 to about 60 minutes.

26. A process according to claim 24 wherein, in step (d), said culture is cooled to a temperature of not more than about 30° C.

27. A process according to claim 24 wherein, in step (d), the pH of said culture is reduced to below about 2.

28. A process according to clai 24 wherein, in step (e), said water-miscible organic solvent is ethanol.

29. A process according to claim 28 wherein, in step (e), from about 2 to about 3 volumes of ethanol are added to each volume of said culture.

30. A process according to claim 24 wherein, in step (e), said water-miscible organic solvent is acetone, methanol or isopropanol.

31. A process according to claim 24 wherein, after step (f), the precipitated polysaccharide is redissolved in water and thereafter there is added to the resultant solution a water-miscible organic solvent in an amount sufficient to reprecipitate said polysaccharide from said solution.

32. A process according to claim 24 wherein, after step (f), the precipitated polysaccharide is redissolved in an aqueous solution of a salt of a metal selected from the group consisting of calcium, sodium, potassium, zinc, copper and ferric iron, and thereafter there is added to the resultant polysaccharide solution a water-miscible organic solvent in an amount sufficient to precipitate a metal salt of the polysaccharide therefrom.

33. A process according to claim 32 wherein said water-miscible organic solvent used to effect said precipitation of said metal salt is ethanol.

34. A process according to claim 33 wherein from about 2 to about 3 volumes of ethanol are added to each volume of the solution containing said polysaccharide and said metal salt.

35. A process according to claim 32 wherein said water-miscible organic solvent used to effect said precipitation of said metal salt is acetone, methanol or isopropanol.

36. A process according to claim 32 wherein said metal is calcium.

37. A process according to claim 36 wherein said metal salt is calcium chloride.

38. A process according to claim 37 wherein said polysaccharide is dissolved in an aqueous solution of calcium chloride, heated to at least 80° C. under agitation and thereafter from about 2 to about 3 volumes of ethanol are added to each volume of said solution to precipitate said metal salt of said polysaccharide therefrom.

* * * * *